United States Patent
Recber et al.

(10) Patent No.: US 9,364,329 B2
(45) Date of Patent: Jun. 14, 2016

(54) CUTTING/BENDING TOOL FOR POLYMER IMPLANT

(71) Applicant: DePuy Synthes Products, Inc., Raynham, MA (US)

(72) Inventors: Ali Cem Recber, West Chester, PA (US); Sean H. Kerr, West Chester, PA (US); James Dwyer, West Chester, PA (US); Christopher Shane, West Chester, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 252 days.

(21) Appl. No.: 13/798,322

(22) Filed: Mar. 13, 2013

(65) Prior Publication Data

US 2013/0304217 A1    Nov. 14, 2013

Related U.S. Application Data

(60) Provisional application No. 61/646,540, filed on May 14, 2012.

(51) Int. Cl.

| | |
|---|---|
| *B26B 17/00* | (2006.01) |
| *A61F 2/28* | (2006.01) |
| *A61B 17/88* | (2006.01) |
| *B26B 11/00* | (2006.01) |
| *B26B 29/02* | (2006.01) |

(52) U.S. Cl.
CPC ........... *A61F 2/2875* (2013.01); *A61B 17/8863* (2013.01); *B26B 17/00* (2013.01); *B26B 11/00* (2013.01); *B26B 29/02* (2013.01)

(58) Field of Classification Search
CPC ................ B26B 11/00; B26B 29/02
USPC .......... 30/123, 128, 142, 145, 146, 299, 134, 30/173, 294; 606/79, 280, 284, 60, 72, 53; 452/6, 1
See application file for complete search history.

(56) References Cited

U.S. PATENT DOCUMENTS

| | | | | |
|---|---|---|---|---|
| 715,315 | A | * 12/1902 | Steinecke | ............... A24F 13/26 144/162.1 |
| 3,972,117 | A | * 8/1976 | Fogg | ............................... 30/287 |

(Continued)

FOREIGN PATENT DOCUMENTS

| | | |
|---|---|---|
| DE | 20208332 | 8/2002 |
| EP | 2204130 | 7/2010 |
| JP | 2003/102743 | 4/2003 |

OTHER PUBLICATIONS

International Patent Application No. PCT/US2013/030678: International Search Report dated Aug. 14, 2013, 18 pages.

(Continued)

*Primary Examiner* — Sean Michalski
*Assistant Examiner* — Liang Dong
(74) *Attorney, Agent, or Firm* — Baker & Hostetler LLP

(57) ABSTRACT

A first tool is configured to cut a polymer implant, and includes a handle, a cutting portion, and a bending portion. A second tool is configured to cut a polymer implant, and includes a handle, a first cutting portion, and a second cutting portion. The cutting portions contain a cutter that is preferably a blade. In the second tool, the blades are preferably angled with respect to each other between about 45°. The tools can be used to reshape an implant that is to be used to replace a portion of a skull.

14 Claims, 10 Drawing Sheets

(56) References Cited

U.S. PATENT DOCUMENTS

| | | | | |
|---|---|---|---|---|
| 4,507,867 A | * | 4/1985 | Haas, Jr. | 30/90.4 |
| D393,776 S | * | 4/1998 | Kessler | D7/401.2 |
| 5,822,865 A | | 10/1998 | Bosch et al. | |
| 6,379,363 B1 | | 4/2002 | Herrington et al. | |
| D616,719 S | * | 6/2010 | Moore | D8/105 |
| 8,382,562 B1 | * | 2/2013 | Lavretsky | A22B 5/0047 452/102 |
| 2003/0208910 A1 | * | 11/2003 | Dudley et al. | 30/314 |
| 2005/0081391 A1 | * | 4/2005 | Denker | B27G 17/04 30/478 |
| 2007/0213713 A1 | | 9/2007 | Capanni | |
| 2009/0222020 A1 | | 9/2009 | Schmuck et al. | |
| 2010/0313428 A1 | | 12/2010 | Mocanu | |

OTHER PUBLICATIONS

International Patent Application No. PCT/US2013/030678: Invitation to Pay Additional Fees dated Jun. 24, 2013, 6 pages.

* cited by examiner

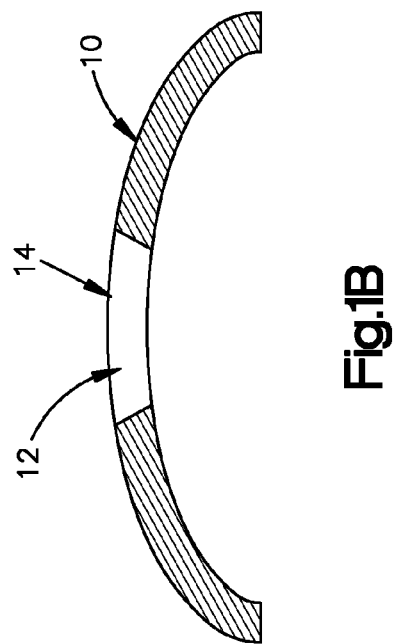
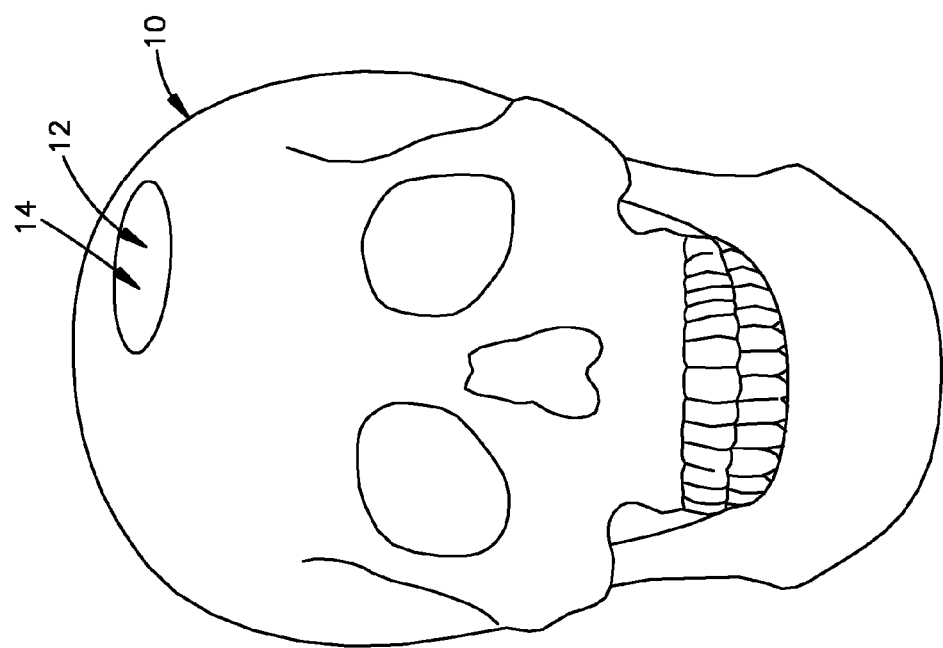

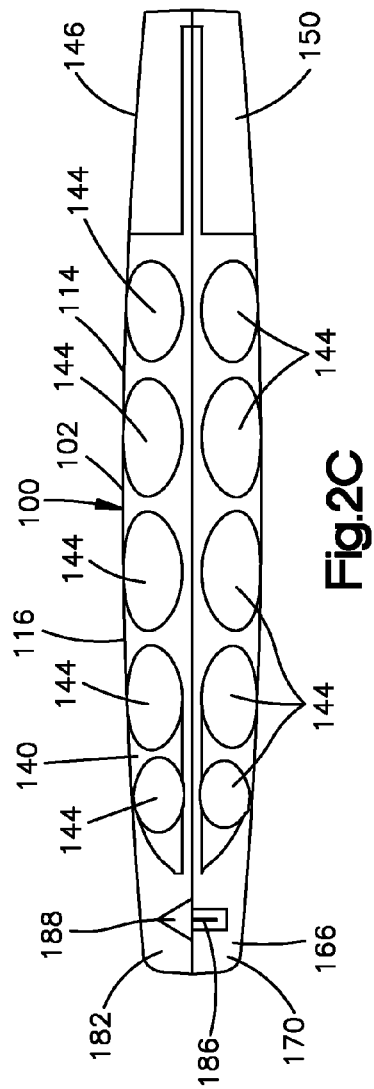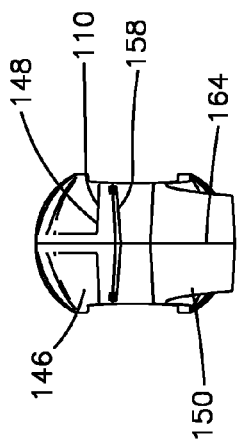

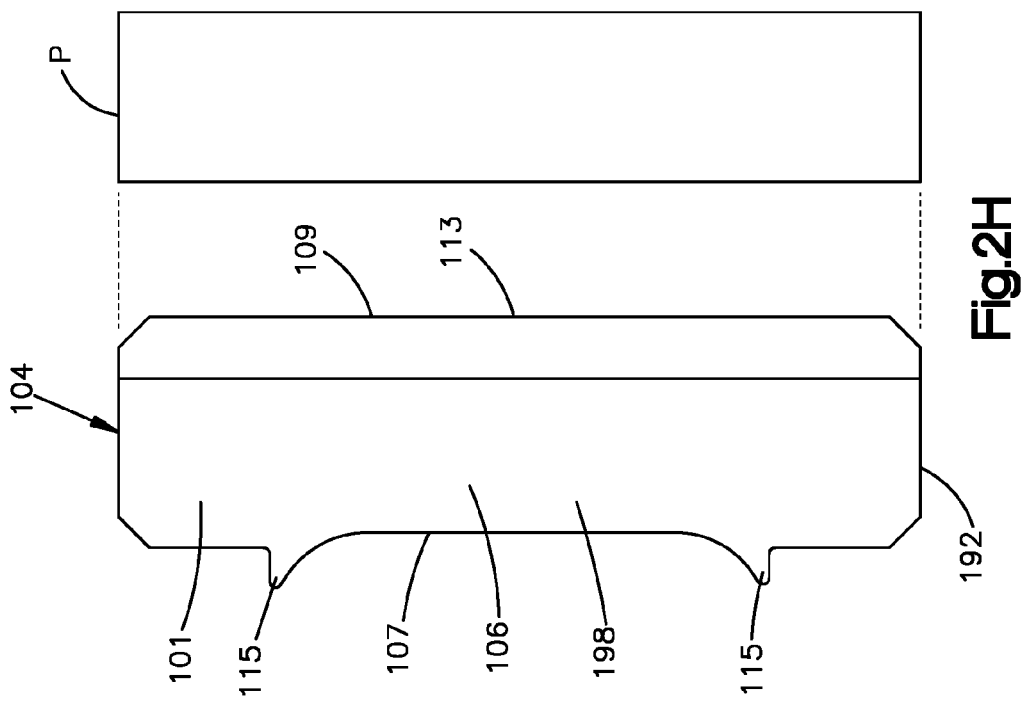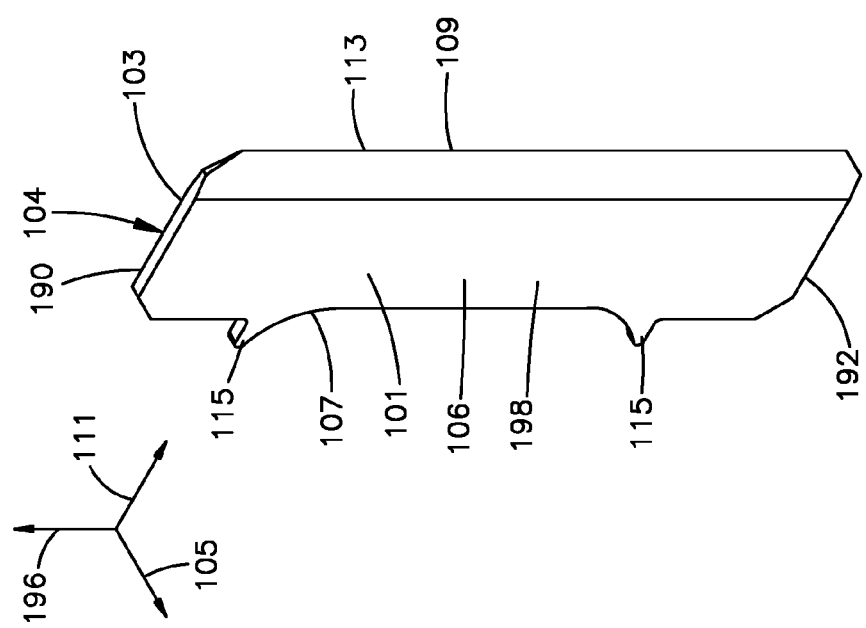

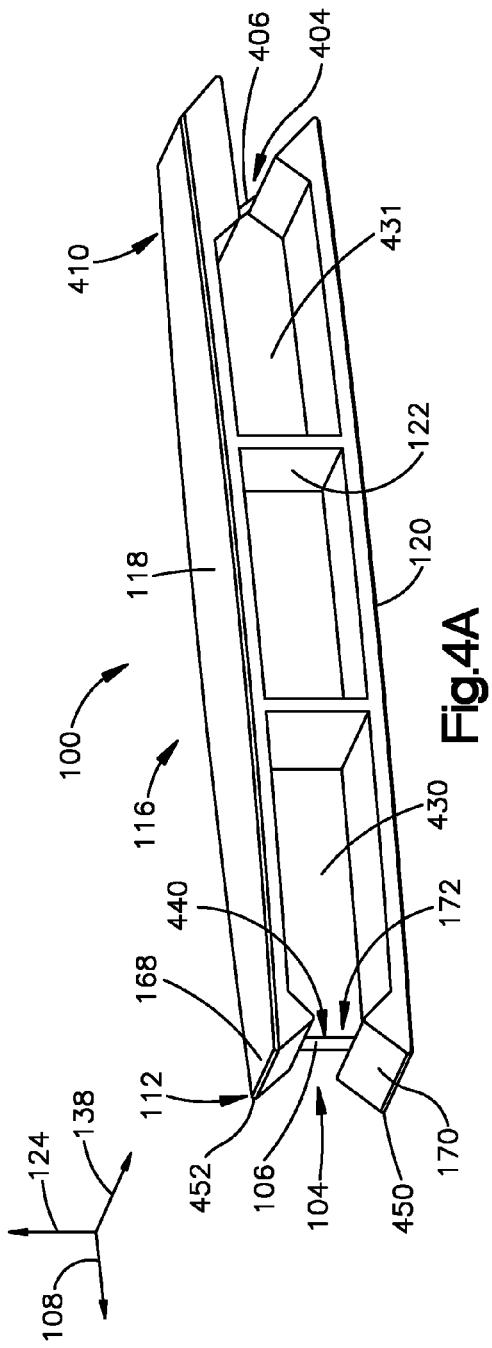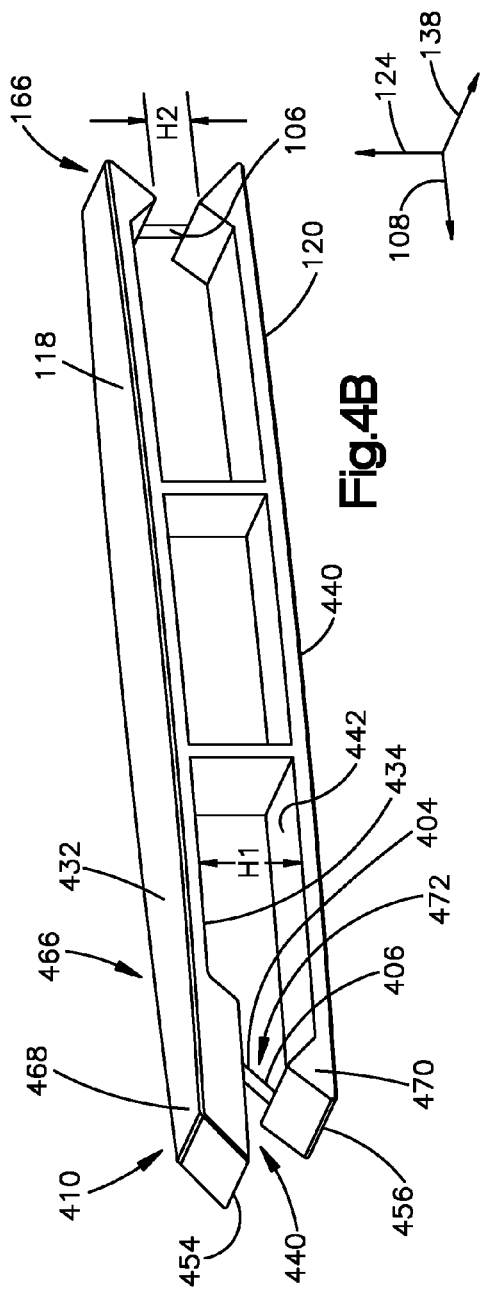

CUTTING/BENDING TOOL FOR POLYMER IMPLANT

CROSS REFERENCE TO RELATED APPLICATIONS

This application claims the benefit of U.S. Provisional Patent Application Ser. No. 61/646,540 filed May 14, 2012, the contents of which are hereby incorporated by reference herein in their entirety.

TECHNICAL FIELD

The present disclosure relates to tools and methods for manipulating orthopedic implants, and more particularly, to tools that are capable of bending and cutting orthopedic implants.

BACKGROUND

Surgeons typically employ craniofacial reconstruction or augmentation to correct craniofacial defects caused by, for example, congenital malformations, traumatic injuries, or disfigurement resulting from cancer surgery. For instance, the craniofacial defect may be an aperture in the skull. The aperture may extend into or through the entire thickness of the skull.

Several surgical procedures have been developed to correct craniofacial defects. For example, an orthopedic implant may be implanted in or over the craniofacial defect. These orthopedic implants may be wholly or partly made of a suitable biocompatible material such as polyethylene or any other suitable polymer. Given that the craniofacial defects as well as the shape and size of the skulls vary from patient to patient, it is difficult to manufacture an orthopedic implant suitable for all craniofacial defects. Instead, orthopedic implants are designed to be cut and shaped to conform to a defect on a case-by-case basis. Thus, it is desirable to trim and shape the orthopedic implants so that the shape and the size of the orthopedic implant substantially match the shape and size of the craniofacial defect.

SUMMARY

The present disclosure relates to tools and method for bending and cutting a polymeric implant having a first size and a first shape. In an embodiment, the tool includes a tool body that includes a bending portion. The bending portion includes a first bending prong and a second bending prong that is spaced from the first bending prong so as to define a first implant-receiving space that is sized to receive at least a portion of the polymeric implant. In operation, a force applied to the bending portion causes the first and second bending prongs to bend the received portion of the polymeric implant to a second shape different than the first shape. The tool further includes a cutting portion that is spaced from the bending portion along the longitudinal direction. The cutting portion includes a first cutting prong and a second cutting prong that is spaced from the first cutting prong so as to define a second implant-receiving space that is sized to receive at least a portion of the polymeric implant. The blade coupled to the tool body, at least a portion of the blade extending into the second implant-receiving space, such that the portion of the implant that is received in the second implant-receiving space can be brought into contact with the blade so as to cut the polymeric implant to a second size different than the first size. The blade may define a cutting edge that is configured to cut the polymeric implant. The blade may be disposed between the first and second cutting prongs at a location inwardly recessed with respect to an outer perimeter of each of the first and second cutting prongs.

In an embodiment, the tool body may be elongate along a first direction. The first and second cutting prongs may be spaced from each other along a second direction that is angularly offset from the first direction. The blade is recessed with respect to the outer perimeter of each of the first and second cutting blades along a third direction that is substantially perpendicular to the first and second directions. The blade is substantially centrally disposed with respect to the first and second cutting prongs along the third direction.

The tool may further include a handle that is connected between the bending portion and the cutting portion. Each of the first bending prong and the second bending prong may protrude from the handle. Each of the first cutting prong and the second cutting prong may protrude from the handle.

The blade may define a substantially planar configuration. Moreover, the blade may include a blade body that extends substantially along a plane. The plane may be oriented substantially normal to the longitudinal direction. The blade may be removably or permanently coupled to the tool body.

In an embodiment, at least one of the first bending prong or the second bending prongs may include teeth that are configured to grip at least a portion of the polymeric implant so as to secure the polymeric implant in the first implant-receiving space. At least one of the first bending prong or the second bending prong is non-linear so that the portion of the polymeric implant received by the bending portion can be brought against the non-linear bending prong so as to impart a non-linear shape to the polymeric implant.

The handle may define a plurality of depressions that extend into the tool body so as to facilitate manual manipulation of the handle by a user. The depressions can also enhance the structural rigidity of the handle. Alternatively, the handle may define a plurality of ribs that protrude from the tool body so as to facilitate manual manipulation of the handle by a user. The ribs can also enhance the structural rigidity of the handle. At least one of the first cutting prong or the second cutting prong may define a hole that is configured and sized to receive at least a portion of the blade so as to couple the blade to the tool body. The tool body may be molded to the blade. The blade may include at least one engagement member that is configured to abut at least one of the first cutting prong or the second cutting prong so as to couple the blade to the tool body.

In an embodiment, the tool includes a cutting portion and a blade. The cutting portion includes a first cutting prong and a second cutting prong that are each elongate along a first direction and spaced from each other along a second direction that is substantially perpendicular to the first direction so as to define an implant-receiving gap, wherein the first and second cutting prongs define respective outer perimeters. The blade defines a cutting surface, the blade attached to at least one of the first and second cutting prongs such that the cutting surface is recessed with respect to the outer perimeters along a third direction that is substantially perpendicular to the first and second directions. The blade may be oriented substantially along a plane that is defined by the second and third directions. The tool may further comprise a bending portion that is coupled to the cutting portion, the bending portion including a first bending prong and a second bending prong that is spaced from the first bending prong along the transverse direction. The bending portion is configured to receive at least a portion of the polymeric implant between the first bending prong and the second bending prong so that a force can be applied to the bending portion while holding polymeric implant to bend the portion of the polymeric implant received by the bending portion.

In a further embodiment, the tool is provided with a cutting portion at both ends instead of having a bending portion at the one end. In this embodiment, the first cutting portion is preferably the above described cutting portion and is preferably oriented such that its cutting edge is in a substantially perpendicular or perpendicular direction to a plane substantially parallel or parallel to the length of the tool. In one embodiment, the polymeric implant cutting tool is configured to cut a polymeric implant where the tool comprises a) a tool body having a length along a first direction and a handle portion comprising an upper handle portion having an outer and an opposing inner surface and a lower handle portion having an outer and an opposing inner surface; b) a first cutting portion located at a distal portion of the tool body, the first cutting portion including a first cutting prong having an end and a first prong inner surface, and a second cutting prong having an end and a second prong inner surface that is spaced from the first prong inner surface along a second direction substantially perpendicular to the first direction, and including a first cutter having a first cutting edge to cut the implant, where the first cutting edge is located longitudinally inward from the end of the first prong; and c) a second cutting portion located at a proximal portion of the tool body, the second cutting portion including a third cutting prong having an end and a third prong inner surface, and a fourth cutting prong having an end and a fourth prong inner surface that is spaced from the third prong inner surface along the second direction, and including a second cutter having a second cutting edge to cut the implant, where the second cutting edge is located longitudinally inward from the end of the third prong; wherein the second cutting edge is positioned at an angle of between 30° and 60° from the first cutting edge. The present invention also provides methods for using the tools to reshape an implant for attachment to the skull of a patient such that the implant forms a portion of the skull.

BRIEF DESCRIPTION OF THE DRAWINGS

The foregoing summary, as well as the following detailed description of a preferred embodiment, are better understood when read in conjunction with the appended diagrammatic drawings. For the purpose of illustrating the invention, the drawings show an embodiment that is presently preferred. The invention is not limited, however, to the specific instrumentalities disclosed in the drawings. In the drawings:

FIG. 1A is a front elevation view of a skull with a defect;

FIG. 1B is a cross-sectional view of a portion of the skull shown in FIG. 1A and the defect;

FIG. 2C is a bottom view of the tool shown in FIG. 2A;

FIG. 2D is a rear elevation view of the tool shown in FIG. 2A;

FIG. 2G is a perspective view of the cutter shown in FIG. 2A;

FIG. 2H is a side elevation view of the cutter shown in FIG. 2G; and

FIGS. 4A-B are perspective views of a tool in accordance with another embodiment of the present disclosure having two cutting portions.

DETAILED DESCRIPTION OF THE DRAWINGS

Figure 1D:
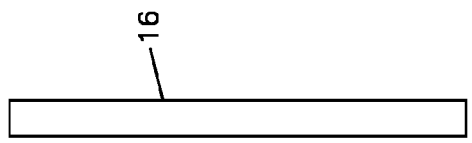
FIG. 1D is a side elevation view of the orthopedic implant of FIG. 1C.
Figure 1E:
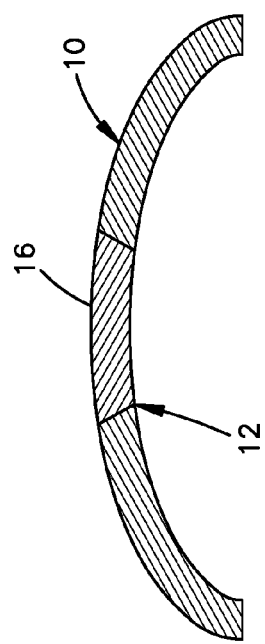
FIG. 1E, is a cross-sectional view of the portion of the skull shown in FIG. 1B with the orthopedic implant shown in FIG. 1C in a second configuration, such as cut and shaped.

Certain terminology is used in the following description for convenience only and is not limiting. The words "right", "left", "lower" and "upper" designate directions in the drawings to which reference is made. The words "proximally" and "distally" refer to directions toward and away from, respectively, the surgeon using the surgical device.

With reference to FIGS. 1A-2A, a tool 100 is configured to cut and bend an implant 16 from a first size and a first shape to a second size and a second shape. For instance, the second size can be less than the first size, and the second shape can have a greater curvature than the first shape. In accordance with certain embodiments, the first shape is substantially planar while the second shape is curved. The second size can correspond generally to the size of a defect 12, which can be an aperture 14 that extends at least into or through a skull 10. The second shape can conform generally to the curvature of the skull 10 and the contour of the defect 12.

As illustrated in FIGS. 2A-H, the tool 100 includes a tool body 102 and a cutter 104 that is configured to be coupled to the tool body 102. The cutter 104 is configured to cut an orthopedic implant, such as the orthopedic implant 16, and can be configured as a blade 106. Irrespective of its configuration, the cutter 104 can make straight or bevel cuts on the orthopedic implant 16 and can be removably or permanently coupled to the tool body 102.

In the depicted embodiment, the tool body 102 can be elongate along a longitudinal direction 108, and defines a first or proximal tool end portion 110, a second or distal tool end portion 112 that is spaced from the first tool end portion 110 along the longitudinal direction, and a third or intermediate tool portion 114 that is disposed between the first tool end portion 110 and the second tool end portion 112. The intermediate end portion 114 can be configured as a handle 116 that facilitate manipulation of the tool 100 by a user. Thus, in operation, the user can easily grab the tool 100 by the handle 116 to bend or cut the orthopedic implant 16. The first tool end portion 110, the second tool end portion 112, and the third tool portion 114 can collectively define a monolithic (one-piece) structure. Alternatively, the tool body 102 can be constructed from several components that are interconnected to one another. Regardless of its construction, the tool body 102 can be entirely or partly made of a substantially rigid material such as a polymer. For example, the tool body 102 can be wholly or partly made of a substantially transparent material such as a suitable transparent polymer. Suitable transparent polymers include, but are not limited to, transparent thermoplastics such as polycarbonate and polymethyl methacrylate (PMMA). The tool body 102 can be made of a substantially transparent material to allow a user to see the location of the cutter 104, and follow the cut being made on the orthopedic implant 16 to be able to adjust the trajectory of the cutter 104 if necessary or desired. In an alternate embodiment, the tool body 102 can be wholly or partly made of a substantially opaque material. For instance, the tool body 102 can be made of a substantially opaque material, and include a window near the cutter 104 for viewing the cutting path. The tool body 102 should be wholly or partly formed of a material having a hardness that is larger than the hardness of the material that forms the orthopedic implant 16.

In the depicted embodiment, the handle 116 may include an upper handle portion 118 and a lower handle portion 120 that is spaced form the upper handle portion 118 along a transverse direction 124. The transverse direction 124 may be substantially perpendicular to the longitudinal direction 108. The handle 116 may further include a handle connection portion 122 disposed between the upper handle portion 118 and the lower handle portion 120. The handle connection portion 122 interconnects the upper handle portion 118 and the lower handle portion 120, and can be elongate along the longitudinal direction 108. In particular, the handle connection portion 122 defines a first or proximal connection end 126 and a second or distal connection end 128 that is spaced from the first connection end 126 along the longitudinal direction 108. The second connection end 128 may define a substantially concave configuration. The first connection end 126 can be coupled and adjacent to the first tool end portion 110, while the second connection end 128 is spaced from the second tool end portion 112 along the longitudinal direction 108 to define an open space 130 between upper handle portion 118 and the lower handle portion 120. The open space 130 allows a user to make deeper cuts with the cutter 104 when the cutter 104 is coupled to the second tool end portion 112. The open space 130 defines a distance H1, such as a height, along the transverse direction 124 that extends from the lower handle portion 120 to the upper handle portion 118. In an embodiment, the distance H1 may range between about 12 millimeters and about 16 millimeters. In one embodiment, the distance H1 may be about 14 millimeters.

With continuing reference to FIG. 2A-H, the upper handle portion 118 may be substantially similar or identical to the lower handle portion 120. The upper handle portion 118 may define an outer surface 132 and an opposed inner surface 134 that is spaced form the outer surface 132 along the transverse direction 124. The inner surface 134 at least partially defines the open space 130. The outer surface 132 of the upper handle portion 118 may have a substantially convex configuration to aid a user to easily grab the handle 116. The handle 116 may further include one or more depressions 136 that extent into the outer surface 132 of the upper handle portion 118. The depressions 136 enhance the ergonomic features of the handle 116, thereby aiding the user to easily grab the handle 116. In addition, the depressions 136 can enhance the structural rigidity of the handle 116. The depressions 136 may be arranged along one or more longitudinal rows that extend along the outer surface 132. For example, in the depicted embodiment, the depressions 136 are arranged in two longitudinal rows. Each longitudinal row includes a plurality of depressions 136 that are spaced from one another along the longitudinal direction 108. One longitudinal row of depressions 136 can be spaced from another longitudinal row along a lateral direction 138. The lateral direction 138 may be substantially perpendicular to the longitudinal direction 108 and the transverse direction 124. At least one depression 136 can be configured as a concavity and may therefore have a substantially concave configuration. For instance, at least one depression 136 can be substantially concave such that it is configured and sized to receive a user's finger. Furthermore, the depressions 136 may be of different sizes and shapes.

As discussed above, the handle 116 may include a lower handle portion 120, which may be substantially similar or identical to the upper handle portion 118. In the depicted embodiment, the lower handle portion 120 defines an outer surface 140 and an opposed inner surface 142. The inner surface 142 at least partially defines the open space 130. The outer surface 140 of the lower handle portion 120 may have a substantially convex configuration to aid a user to easily grab the handle 116. The handle 116 may further include one or more depressions 144 that extend into the outer surface 140 of the lower handle portion 120. The depressions 144 enhance the ergonomic features of the handle 116, thereby aiding the user to easily grab the handle 116. The depressions 144 may be arranged along one or more longitudinal rows that extend along the outer surface 140. For example, in the depicted embodiment, the depressions 144 are arranged in two longitudinal rows. Each longitudinal row includes a plurality of depressions 144 that are spaced from one another along the longitudinal direction 108. One longitudinal row of depressions 144 can be spaced from another longitudinal row of depressions 144 along the lateral direction 138. At least one depression 144 can be configured as a concavity and may therefore have a substantially concave configuration. For example, at least one depression 144 can be substantially concave such that it is configured and sized to receive a user's finger. Further, the depressions 144 may be of different sizes and shapes.

With continuing reference to FIG. 2A-H, the first tool end portion 110 of the tool body 102 may be configured as a bending portion 146 that is configured to bend and contour an orthopedic implant such as the orthopedic implant 16. In the depicted embodiment, the bending portion 146 includes a first bending prong 148 and a second bending prong 150 that is spaced from the first bending prong along the transverse direction 124. Each of the first bending prong 148 and the second bending prong 150 protrudes from intermediate end portion 114 in a proximal direction 152 that is opposite the longitudinal direction 108. The first bending prong 148 and the second bending prong 150 define a first implant receiving space 154 between them. The first implant receiving space 154 can be configured and sized to receive an orthopedic implant such as the orthopedic implant 16. In operation, the first bending prong 148 and the second bending prong 150 can be configured to hold at least a portion of the orthopedic implant 16 such that the handle 116 of the tool 100 can be used as a lever to bend the orthopedic implant 16.

The first bending prong 148 defines an first outer bending surface 156 and an opposed first inner bending surface 158 that is spaced from the first outer bending surface 156 along the transverse direction 124. The first inner bending surface 158 is configured to contact the orthopedic implant 16. The first bending prong 148 may include one or more teeth 160 that protrude from the first inner bending surface 158 in a direction toward the first implant receiving space 154 (i.e., in a direction opposite the transverse direction 124). In the depicted embodiment, the first bending prong 148 includes a plurality of teeth 160 that are spaced from one another along the longitudinal direction 108. The teeth 160 are configured to engage the orthopedic implant 16 to hold onto the orthopedic implant 16 while the orthopedic implant 16 is being bent with the bending portion 146. Hence, the one or more teeth 160 can be obliquely angle relative to the first inner bending surface 158 toward the handle 116 so as to prevent, or at least inhibit, the orthopedic implant 16 disposed in the bending portion 146 from slipping out of the first implant receiving space 154 while orthopedic implant 16 is being bent with the bending portion 146. The first bending prong 148 defines a plurality of indentations between the teeth 160 that orthopedic implant 16 to be caught at different positions along the first inner bending surface 158 so that the fulcrum of the levering action performed during bending can be adjusted to achieve the desired contour. In an alternative embodiment, the second bending prong 150 may include teeth that are configured to engage the orthopedic implant 16.

The second bending prong 150 defines a second outer bending surface 162 and an opposed second inner bending surface 164 that is spaced from the second outer bending surface 162 along the transverse direction 124. The second outer bending surface 162 may have a substantially curved configuration (or any other non-linear configuration) such that it is configured to receive a user's finger such as a thumb. For example, the curved configuration of the second outer bending surface 162 can substantially match the curved configuration of an extended thumb so that the user can apply a force to the bending portion 146 in order to bend a portion of an orthopedic implant that is disposed in the first implant receiving space 154 while holding (for example with the hand) another portion of the orthopedic implant. The second inner bending surface 164 may also have a substantially curved configuration (or any non-linear configuration) so that a portion of the orthopedic implant 16 that is disposed in the first implant receiving space 154 can be brought against the non-linear bending prong 150 so as to impart a non-linear shape to the polymeric implant. Alternatively, the second inner bending surface 164 does not necessarily have a curved configuration. In an alternate embodiment, the teeth can protrude from the second bending prong 150, and the first bending prong 148 can have a substantially curved configuration. In addition, at least one of the first inner bending surface 158 or the second inner bending surface 164 can be configured as textured surface to prevent, or hinder, slippage of the orthopedic implant 16 that is at least partially disposed in the implant receiving space 154.

In operation, the bending portion 146 is configured to bend at least a portion of the orthopedic implant 16 or any other suitable implant. To do so, a portion of the orthopedic implant 16 is disposed in the implant receiving space 154. The first bending prong 148 can be advanced toward the orthopedic implant 16 so that the teeth 160 contact the orthopedic implant 16 to secure the orthopedic implant 16 in the implant receiving space 154. Another portion of the orthopedic implant 16 that is not disposed in the first implant receiving space 154 is held in place. For example, the user can manually hold the portion of the orthopedic implant 16 that is not disposed in the implant receiving space 154. Then, a force can be applied on the second outer bending surface 162 while holding the portion of the orthopedic implant 16 that is not disposed in the first implant receiving space 154 in place such that the tool 100 acts as a lever and bends the portion of the orthopedic implant 16 that is disposed in the implant receiving space 154.

With continuing reference to FIG. 2A-H, the second tool end portion 112 of the tool body 102 can be configured as a cutting portion 166. The cutting portion 166 can be configured to cut the orthopedic implant 16 or any other suitable implant. In particular, the cutting portion 166 can be configured to make straight, curved, or bevel cuts on the orthopedic implant 16. In the depicted embodiment, the cutting portion 166 includes a first cutting prong 168 and a second cutting prong 170 that is spaced from the first cutting prong along the transverse direction 124. Each of the first cutting prong 168 and the second cutting prong 170 can protrude from the handle 116 in the longitudinal direction 108. That is, the first cutting prong 168 and the second cutting prong 170 can each protrude from the handle 116 in a distal direction. In the depicted embodiment, the first cutting prong 168 and the second cutting prong 170 may define a substantially curved configuration so that the cutting portion 166 defines a neck region where the first cutting prong 168 is closest to the second cutting prong 170. The neck region between the first cutting prong 168 and the second cutting prong 170 defines a second implant receiving space 172 that is configured and sized to receive at least a portion of the cutter 104. The second implant receiving space 172 defines a distance H2, such as a height, along the transverse direction 124 that extends from the first cutting prong 168 to the second cutting prong 170. The distance H1 is larger than the distance H2. For example, the distance H2 may range between about 6.25 millimeters and about 8.25 millimeters. In one embodiment, the distance H2 may be about 7.25 millimeters. In this embodiment, the cutting portion 166 can be configured to cut orthopedic implants 16 that are at most 7 millimeters thick. However, the distance H2 may vary. Also, the distance H2 is small enough to prevent, or at least inhibit, a user's finger to be introduced into the second implant receiving space 172, thereby minimizing the risk that the user would be injured by the cutter 104. The curved configuration of the first cutting prong 168 and the second cutting prong 170 provides enough clearance to allow the cutter 104 to make straight, curved, or bevel cuts on the orthopedic implant 16.

The first cutting prong 168 defines a first outer prong surface 174 and an opposed first inner prong surface 176 that is spaced from the first outer prong surface 174 along the transverse direction 124. In addition, the cutting portion 166 may further define a first hole 178 that extends through the first cutting prong 168. In particular, the first hole 178 may extend through the first outer prong surface 174 and the first inner prong surface 176. The first hole 178 can be configured and sized to receive at least a portion of the cutter 104, which can be constructed as the blade 106. The first cutting prong 168 may further include a first indicator 180 that is configured to indicate the user the position or direction of the cutting edge of the cutter 104. In the depicted embodiment, the indicator 180 can be configured as an embossed arrow disposed on the first outer prong surface 174. The embossed arrow can be disposed over the first hole 178. In addition, the first cutting prong 168 defines a first lateral surface 169 and a second lateral surface 171 that is spaced from the first lateral surface along the lateral direction 138.

The second cutting prong 170 defines a second outer prong surface 182 and an opposed second inner prong surface 184 that is spaced from the second outer prong surface 182 along the transverse direction 124. Moreover, the cutting portion 166 may further define a second hole 186 that extends through the second cutting prong 170. The second hole 186 may extend through the second outer prong surface 182 and the second inner prong surface 184. In particular, the second hole 186 can be configured and sized to receive at least a portion of the cutter 104, which can be constructed as the blade 106. The second cutting prong 170 may further include a second indicator 188 that is configured to indicate the user the position or direction of the cutting edge of the blade 106. In the depicted embodiment, the indicator 188 can be configured as an embossed arrow disposed on the second outer prong surface 182. The embossed arrow can be disposed over the second hole 186. The second cutting prong 170 defines a first lateral surface 173 and a second lateral surface 175 that is spaced from the first lateral surface 173 along the lateral direction 138.

With continuing reference to FIG. 2A-H, the cutting portion 166 includes the cutter 104. The first cutting prong 168 and the second cutting prong 170 are configured to collectively support the cutter 104. As discussed above, the cutter 104 can be configured as a blade 106. Irrespective of its configuration, the cutter 104 can cut through a polymeric implant such as the orthopedic implant 16. The cutter 104 can be made of a material that can cut through a polymer implant such as the orthopedic implant 16. For instance, the blade 106 may be wholly or partly made of a suitable metal such as stainless steel. Regardless of the specific material used, the blade 106 should be wholly or partly made from a material that has a hardness that is larger than the hardness of orthopedic implant 16.

In the depicted embodiment, the blade 106 can define a substantially planar configuration that extends along a plane P. When the blade 106 is coupled to the tool body 102, the plane P may be oriented substantially normal to the longitudinal direction 108, and substantially parallel to the lateral direction 138. Alternatively, when the blade 106 is coupled to the tool body 102, the plane P may be oriented substantially normal to the lateral direction 138 and substantially parallel to the longitudinal direction 108. The blade 106 includes a blade body 198 that defines an upper blade portion 190 and an opposed lower blade portion 192 that is spaced from the upper blade portion 190 along a transverse direction 196. When the blade 106 is coupled to the tool body 102, the transverse direction 196 may substantially coincide with the transverse direction 124. In the depicted embodiment, the blade body 195 may be elongate along the transverse direction 196. The blade body 198 further defines a first blade side surface 101 and an opposed second blade side blade 103 that is spaced from the first blade side surface 101 along a longitudinal direction 105. When the blade 106 is coupled to the tool body 102, the longitudinal direction 105 may substantially coincide with the longitudinal direction 108. The blade body 198 may further define a first blade end 107 and an opposed second blade end 109 that is spaced from the first blade end 107 along a lateral direction 111. When the blade 106 is coupled to the tool body 102, the lateral direction 111 may substantially coincide with the lateral direction 138. In the depicted embodiment, when the blade 106 is coupled to the tool body 102, the blade 106 may be spaced from the first lateral surface 169 and the second lateral surface 171 of the first cutting prong 168 along the lateral direction 138. In the depicted embodiment, when the blade 106 is coupled to the tool body 102, the blade 106 may be spaced from the first lateral surface 173 and the second lateral surface 175 along the lateral direction 138.

The blade body 198 may include a tapered portion so as to define a substantially sharp cutting edge 113 at the second blade end 109. Alternatively or additionally, the blade body 198 may include another substantially sharp cutting edge at the first blade end 107. Thus, the cutter 104 can be configured as a double edge blade to facilitate cutting in at least two directions. The blade 106 may further include one or more blade engagement members 115 that are configured to engage at least a portion of the tool body 102 so as to couple the blade 106 to the tool body 102. At least one of the engagement members 115 can be constructed as a catch or a hook. In the depicted embodiment, the blade 106 may include two blade engagement members 115 that protrude from the blade body 198 in opposite to the lateral direction 111. Specifically, the engagement members 115 may be spaced from each other along the transverse direction 196, and may protrude from the first blade end 107 of the blade body 198. No portion of the cutting edge 113 is disposed beyond the outer boundaries of the cutting portion 166 to protect a user from injury. That is, the blade 106 may be disposed between the first and second cutting prongs 168, 170 at a location inwardly recessed with respect to an outer perimeter of each of the first and second cutting prongs. The blade 106 may be substantially centrally disposed with respect to the first and second cutting prongs 168, 170 along the lateral direction 138. The entire cutting edge 113 may be disposed between the first lateral surface 169 and the second lateral surface 171 of the first cutting prong 168. Additionally or alternatively, the entire cutting edge 113 may be disposed between the first lateral surface 173 and the second lateral surface 175 of the second cutting prong 170. However, at least a portion of the cutting edge 113 may extend beyond the outer boundaries of the cutting portion 166 in order to make steeper cut angles while trimming the polymeric implant. That is, at least a portion of the cutting edge 113 may be exposed.

In the depicted embodiment, the blade 106 can be coupled to the tool body 102 by inserting the lower blade portion 192 in the second hole 186, and by inserting the upper blade portion 190 in the first hole 178. When the blade 106 is partially inserted through the first hole 178 and the second hole 1896, at least one engagement member 115 abuts the first inner prong surface 176, and at least another engagement member 115 abuts the second inner prong surface 184 so that the blade 106 is coupled to the tool body 102 and at least a portion of the blade 106 is disposed between the first cutting prong 168 and the second cutting prong 170. In an alternate embodiment, the tool body 102 can be injected molded, and the blade 106 can be insert molded to the tool body 102. For example, the blade 106 can be inserted into a mold, and a polymer can be molded over the blade 106 to form the tool body 102. Thus, blade 106 can be permanently coupled to the tool body 102. Alternatively, the blade 106 can be removably coupled to the tool body 102.

To cut a polymeric implant with the tool 100, the polymeric implant can be placed in the second implant receiving space 172, and then a translation force is applied to the tool 100 to move the cutter 104 toward the polymer implant to cut said implant. The user may manually hold the implant while advancing the cutter 104 through the implant to make the cut. It is envisioned that the user may alternate between cutting and bending to produce an implant with the desired shape and contour.

Figure 1C:
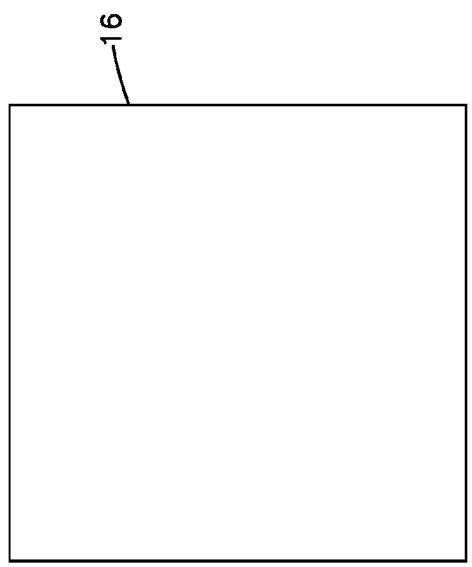
FIG. 1C is a front elevation view of an orthopedic implant shown in a first, or initial, configuration.
Figure 2A:
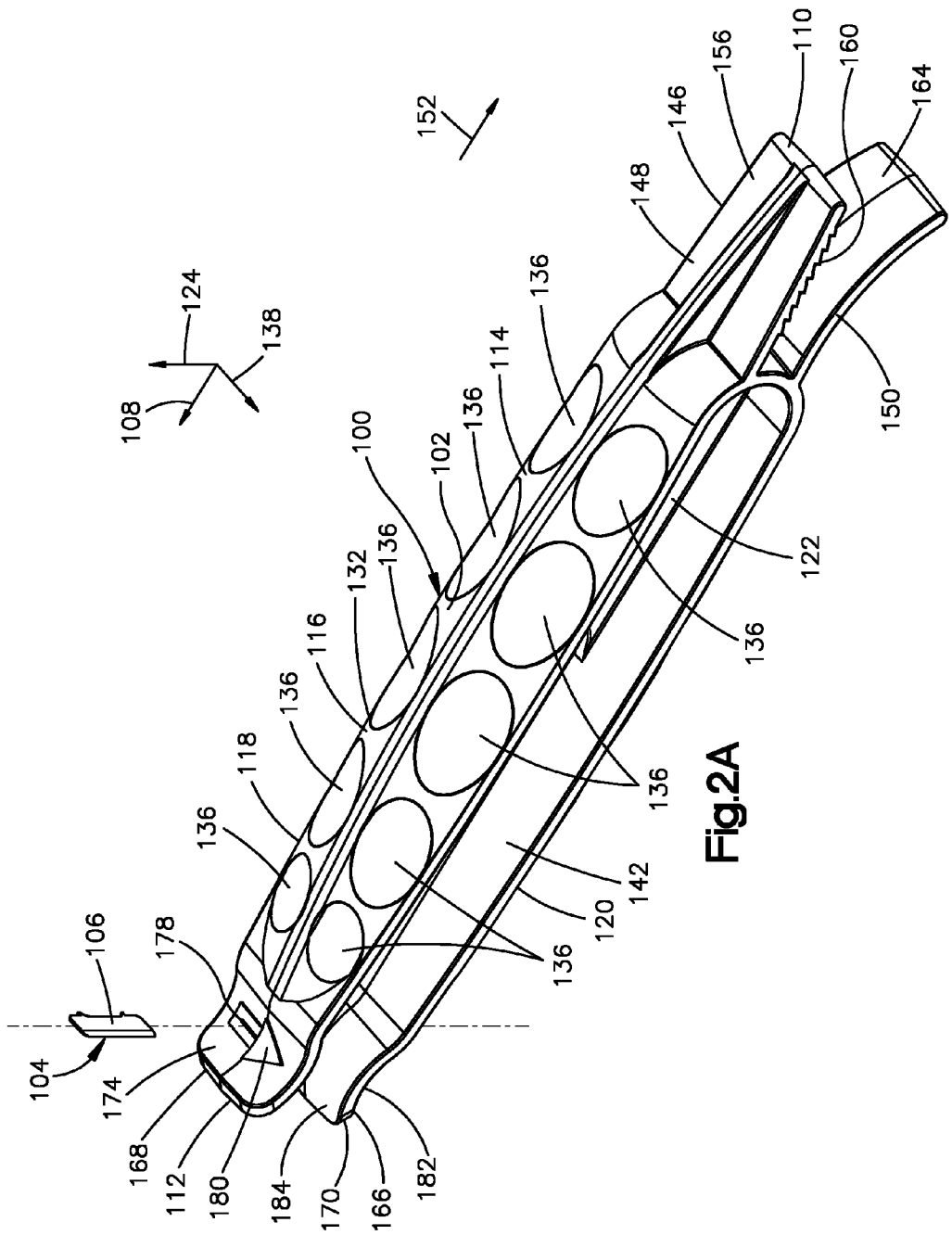
FIG. 2A is a perspective exploded view of a tool that is configured to cut and bend an implant from the first configuration illustrated in FIG. 1C to the second configuration shown in FIG. 1E, the tool including a tool body and a cutter supported by the tool body.
Figure 2B:
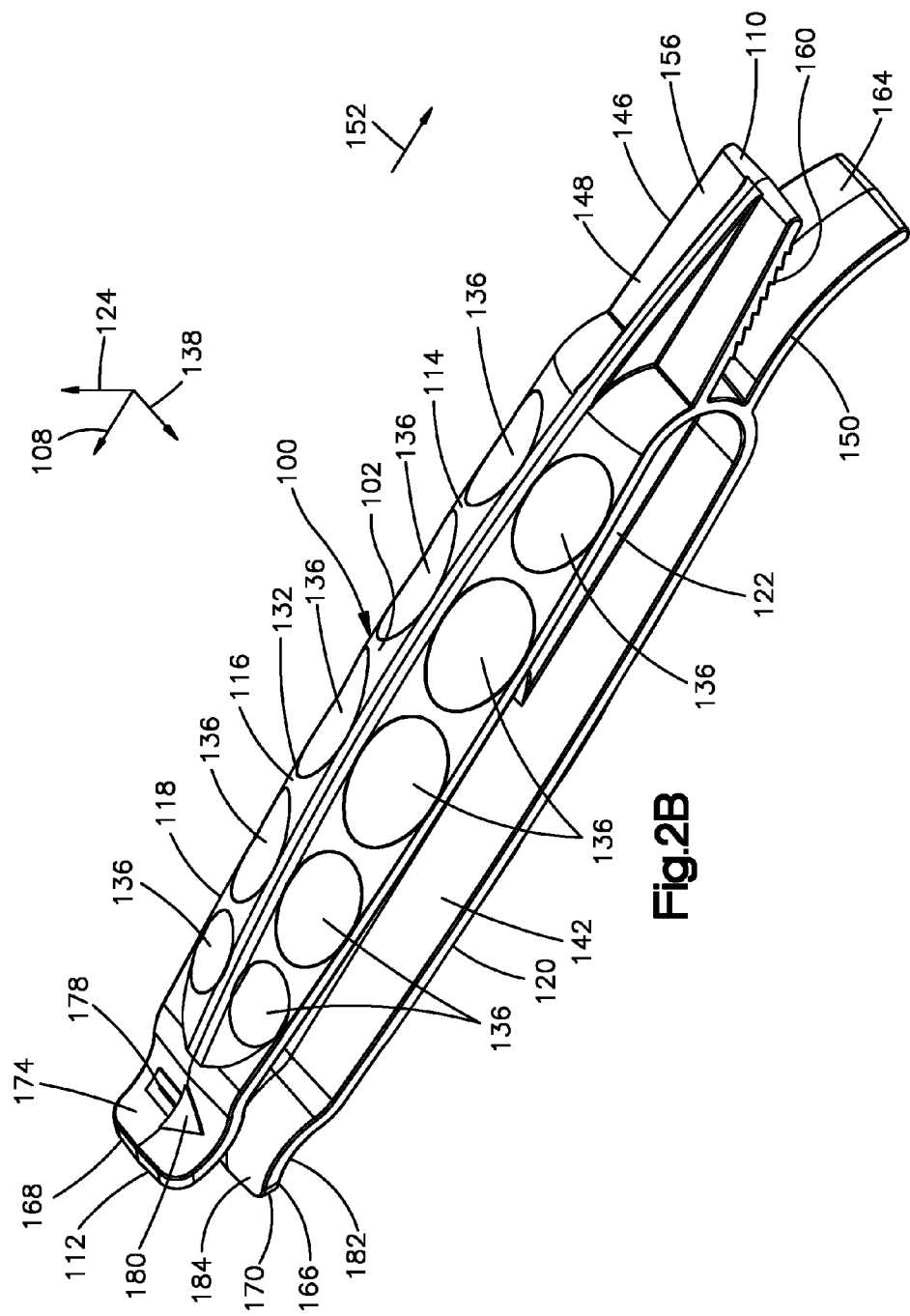
FIG. 2B is a perspective view of the tool shown in FIG. 2A.
Figure 2E:
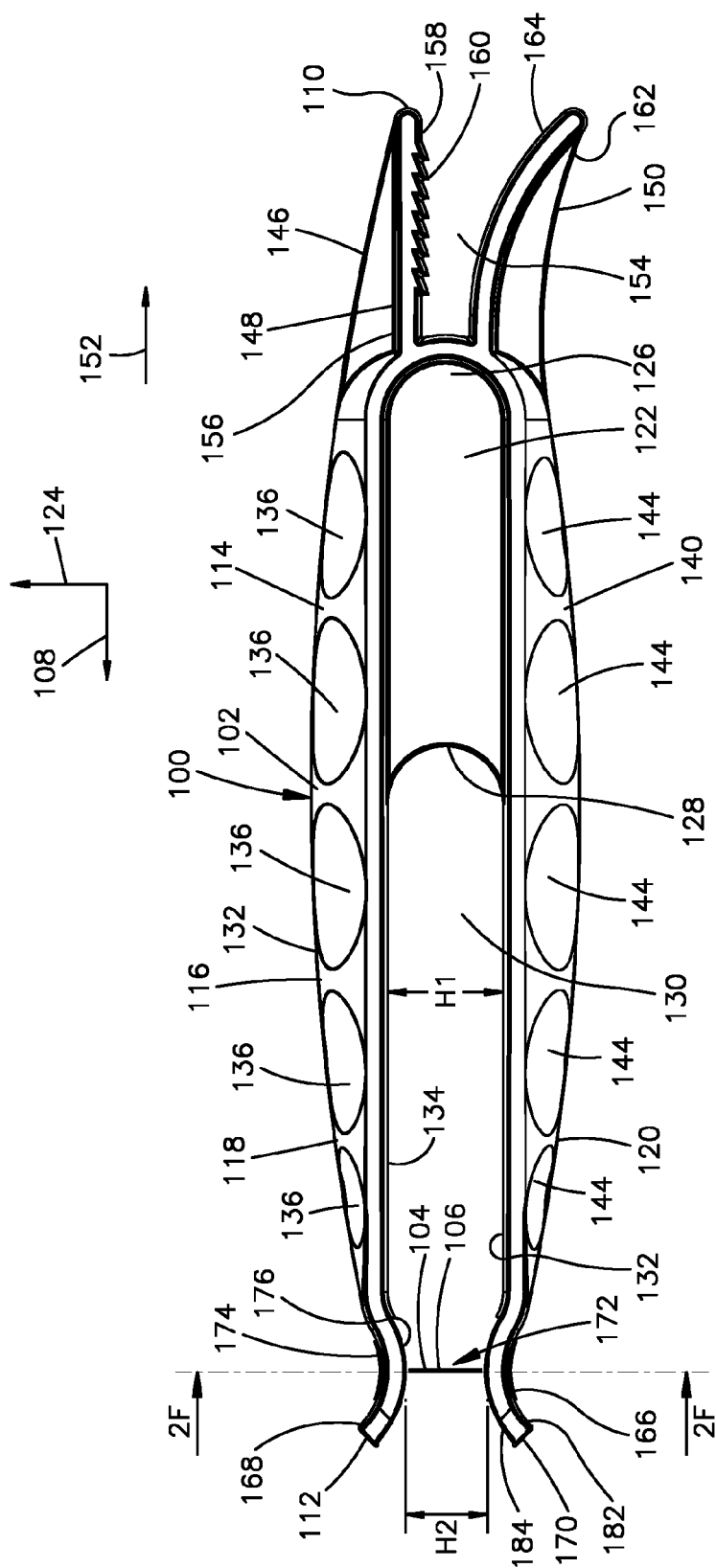
FIG. 2E is a side elevation view of the tool shown in FIG. 2A.
Figure 2F:
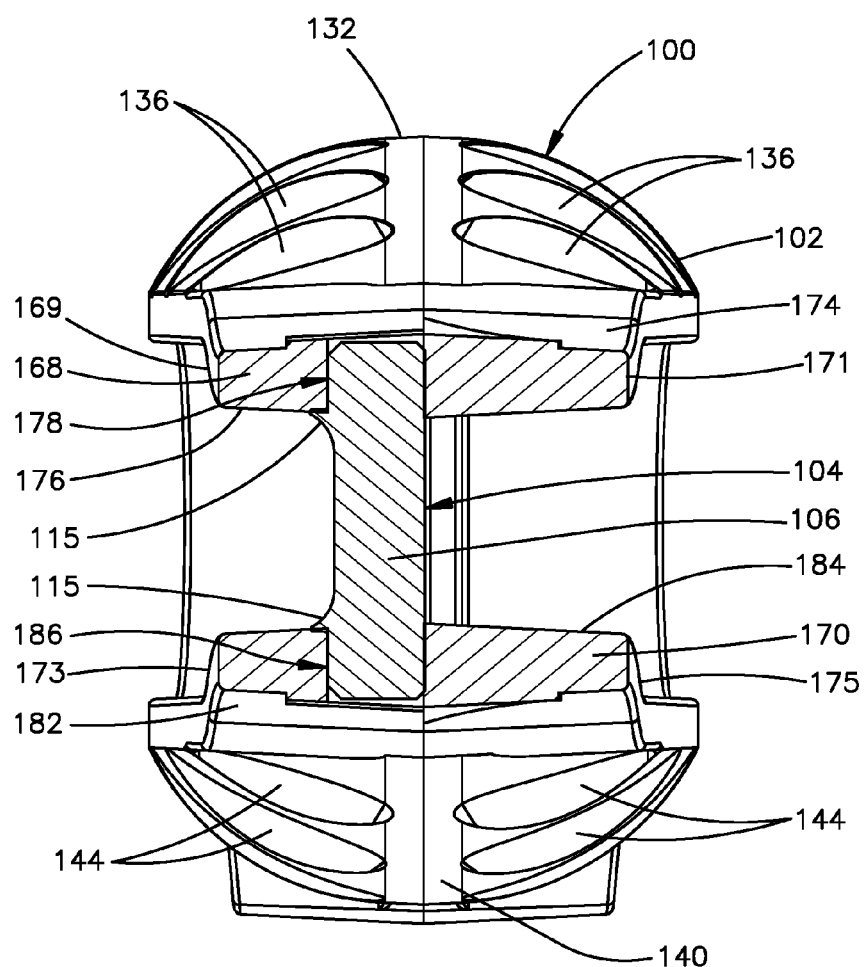
FIG. 2F is a cross-sectional view of the tool shown in FIG. 2A, taken along section line 2F-2F of FIG. 2E.
Figure 3:
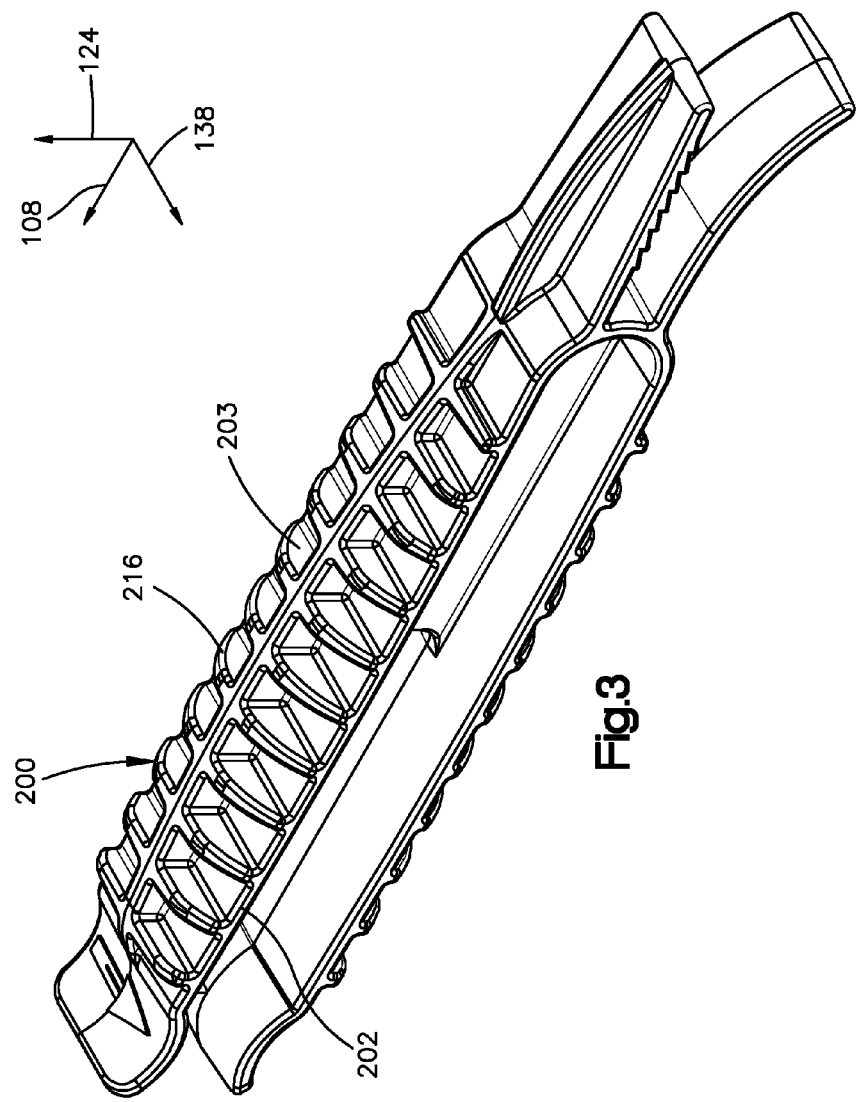
FIG. 3 is a perspective view of a tool in accordance with another embodiment of the present disclosure.

With reference to FIG. 3, a tool 200 is configured to cut and bend a polymeric implant such as the orthopedic implant 16 illustrated in FIG. 1C. The tool 200 can be substantially similar to the tool 100 illustrated in FIG. 2A. In this embodiment, the handle 216 of the tool 200 includes one or more protrusions 201 instead of depressions 136. In the depicted embodiment, the protrusions 201 protrude from the tool body 202, and may be configured as ribs 203. The ribs 203 may be spaced apart from one another along the longitudinal direction 108, and are configured to enhance the ergonomic features of the handle 216, thereby aiding the user to easily grab the handle 216. In addition, the ribs 203 can enhance the structural rigidity of the handle 216. It is envisioned that the tool may include both depressions 136 and protrusions 201.

In another embodiment the tool 100 can be constructed such that it contains a cutter 104 at both ends and does not include a bending portion. As depicted in FIGS. 4A-B, the tool 100 can be constructed such that there is a distal tool end portion 112 that has a first blade 106 that functions as a first cutter 104 and also there is a proximal tool end portion 410 that has a second blade 406 that functions as a second cutter 404. The first cutter 104 is similar to the above-described cutter 104 depicted in FIGS. 2A-H and 3. In the depicted embodiment, the tool body 102 can be elongate along a longitudinal direction 108. The handle 116 facilitates manipulation of the tool 100 by a user. The tool 100 of this embodiment can be constructed of the same materials and in the same fashion as the tool depicted in FIGS. 2A-H.

In the depicted embodiment, the handle 116 may include an upper handle portion 118 and a lower handle portion 120 that is spaced form the upper handle portion 118 along a transverse direction 124. The transverse direction 124 may be substantially perpendicular to the longitudinal direction 108. The handle 116 may further include one or more handle connection portions 122 disposed between the upper handle portion 118 and the lower handle portion 120. The handle connection portions 122 interconnect the upper handle portion 118 and the lower handle portion 120, and can have a narrow or elongated length along the longitudinal direction 108, a width that is partially or fully extending along the width of the upper and lower handle portions 118, 120 in the lateral direction 138, and a height along the transverse direction 124. The handle connection portions 122 can be one, two, three, or more in number, and can have the same or different lengths and widths. It is preferred that the handle connection portion(s) 122 are constructed such that they define an open spaces 430, 431 between upper handle portion 118 and the lower handle portion 120. The open spaces 430, 431 allow a user to make deeper cuts with the blades 106, 406. The open spaces 430, 431 define a distance H1, such as a height, along the transverse direction 124 that extends from an inner surface 420 of the lower handle portion 120 to an inner surface 418 of the upper handle portion 118. In an embodiment, the distance H1 may range between about 12 millimeters and about 16 millimeters. In one embodiment, the distance H1 may be about 14 millimeters.

With continuing reference to FIGS. 4A-B, the upper handle portion 118 may be substantially similar or identical to the lower handle portion 120. The upper handle portion 118 may define an outer surface 432 and an opposed inner surface 434 that is spaced form the outer surface 432 along the transverse direction 124. The inner surface 434 at least partially defines the open spaces 430, 431. The outer surface 432 of the upper handle portion 118 may have take various forms, such as a planar surface or a substantially convex configuration (like FIG. 2A) to aid a user to easily grab the handle 116 (and be constructed as described above for the handle 116 for the embodiment in FIGS. 2A-H). As discussed above, the handle 116 may include a lower handle portion 120, which may be substantially similar or identical to the upper handle portion 118. In the depicted embodiment, the lower handle portion 120 defines an outer surface 440 and an opposed inner surface 442. The inner surface 442 at least partially defines the open space 430, 431.

With continuing reference to FIGS. 4A-B, the second tool end portion 112 can be configured as a cutting portion as described above for the embodiment depicted in FIGS. 2A-H. The first cutting portion 166 can be configured to cut the orthopedic implant 16 or any other suitable implant. In particular, the first cutting portion 166 can be configured to make straight, curved, or bevel cuts on the orthopedic implant 16. In the depicted embodiment, the cutting portion 166 includes a first cutting prong 168 and a second cutting prong 170 that is spaced from the first cutting prong 168 along the transverse direction 124. Each of the first cutting prong 168 and the second cutting prong 170 can protrude from the handle 116 in the longitudinal direction 108. That is, the first cutting prong 168 and the second cutting prong 170 can each protrude from the handle 116 in a distal direction. In the depicted embodiment, the first cutting prong 168 and the second cutting prong 170 may define a reduced height portion on one or both sides longitudinally from the blade 106, such as by way of a slanted, or other geometry such as curved, configuration so that the first cutting portion 166 defines a neck region 440 where the inner surface of the first cutting prong 168 is closest to the inner surface of the second cutting prong 170. The neck region 440 between the first cutting prong 168 and the second cutting prong 170 defines a second implant receiving space 172 that is configured and sized to receive at least a portion of the blade 106. That is, it is preferred that the tool 100 be designed such that the blade 106 is retained a longitudinal distance from the ends 450, 452 of the second and first prongs 170, 168, respectively, to act as a safety feature to retain the blade 106 within the tool. Preferably, the second implant receiving space 172 defines a distance H2, such as a height, along the transverse direction 124 that extends from the inner surface of the first cutting prong 168 to the inner surface of the second cutting prong 170, preferably where the blade 106 attaches to the prongs. The distance H1 is larger than the distance H2. For example, the distance H2 may range between about 6.25 millimeters and about 8.25 millimeters. In one embodiment, the distance H2 may be about 7.25 millimeters. In this embodiment, the cutting portion 166 can be configured to cut orthopedic implants 16 that are at most 7 millimeters thick. However, the distance H2 may vary. Also, the distance H2 is small enough to prevent, or at least inhibit, a user's finger to be introduced into the second implant receiving space 172, thereby minimizing the risk that the user would be injured by the cutter 104. The first and second prongs 168, 170 can be constructed as described above for the prior embodiments. The cutter 104 can be constructed as described above for the prior embodiments. The blade 106 can be constructed and oriented as described above for the prior embodiments. The blade 106 is also positioned back away from the end of the prongs 168, 170 such that the cutting edge of the blade is from about 3 to about 20 mm, preferably from about 5 to about 15 mm, and more preferably from about 5 to about 12 mm, and in some cases about 6-8 mm from the end of the prongs.

With continuing reference to FIGS. 4A-B, the first tool end portion 410 can be configured as a second cutting portion 466. The second cutting portion 466 can be configured to cut the orthopedic implant 16 or any other suitable implant. In particular, the second cutting portion 466 can be configured to make straight, curved, or bevel cuts on the orthopedic implant 16. In the depicted embodiment, the cutting portion 466 includes a third cutting prong 468 and a fourth cutting prong 470 that is spaced from the third cutting prong 468 along the transverse direction 124. Each of the third cutting prong 468 and the fourth cutting prong 470 can protrude from the handle 116 in the longitudinal direction 108. That is, the third cutting prong 468 and the fourth cutting prong 470 can each protrude from the handle 116 in a distal (longitudinal) direction. In the depicted embodiment, the third cutting prong 468 and the fourth cutting prong 470 may define a reduced height portion on one or both sides longitudinally from the blade 406; such as by way of a slanted, or other geometry such as curved, configuration so that the cutting portion 466 defines a neck region 440 where the inner surface of the third cutting prong 468 is closest to the inner surface of the second cutting prong 470. The neck region 440 between the third cutting prong 468 and the fourth cutting prong 470 defines a third implant receiving space 472 that is configured and sized to receive at least a portion of the blade 406. That is, it is preferred that the tool 100 be designed such that the blade 406 is retained a longitudinal distance from the ends 454, 456 of the third and fourth prongs 468, 470 to act as a safety feature to retain the blade 406 within the tool. Preferably, the third implant receiving space 472 defines a distance H2, such as a height, along the transverse direction 124 that extends from the inner surface of the first cutting prong 468 to the inner surface of the second cutting prong 470, where H2 is preferably located where the blade 406 attaches to the cutting prongs. The distance H1 is larger than the distance H2. For example, the distance H2 may range between about 6.25 millimeters and about 8.25 millimeters. In one embodiment, the distance H2 may be about 7.25 millimeters. In this embodiment, the cutting portion 466 can be configured to cut orthopedic implants 16 that are at most 7 millimeters thick. However, the distance H2 may vary. Also, the distance H2 is small enough to prevent, or at least inhibit, a user's finger to be introduced into the third implant receiving space 472, thereby minimizing the risk that the user would be injured by the blade 406. The third and fourth prongs 468, 470 can be constructed as described above for the first and second prongs. The cutter 404 can be constructed as described above for the cutter 104. The blade 406 is also positioned back away from the end of the prongs 468, 470 such that the cutting edge of the blade is from about 3 to about 20 mm, preferably from about 5 to about 15 mm, and more preferably from about 5 to about 12 mm, and in some cases about 6-8 mm from the end of the prongs.

The blade 406 can be constructed from the same materials and in the same manner as described above for blade 106. As shown in FIGS. 2G-H, the blade 406, like blade 106, can define a substantially planar configuration that extends along a plane P. It a preferred embodiment, as depicted in FIGS. 4A-B, blade 106 is preferably coupled to the tool body 102 such that the plane P may be oriented substantially normal to the longitudinal direction 108, and substantially parallel to the lateral direction 138. Alternatively, when the blade 106 is coupled to the tool body 102, the plane P may be oriented substantially normal to the lateral direction 138 and substantially parallel to the longitudinal direction 108. Thus, the blade 106 is preferably designed such that its cutting edge is substantially perpendicular to the length of the tool; that is, a plane that runs substantially parallel to the length of the tool would be substantially perpendicular to the plane P for the blade 106. It is preferred that the blade 406 then be positioned such that its plane P, which defines its cutting edge, is at an angle of about 30-60°, about 35-55°, about 40-50°, and more preferably about 45° to the length of the tool, that is, to a plane that runs substantially parallel to the length of the tool. In this regard, the plane P for the blade 406 would be at an angle of about 30-60°, about 35-55°, about 40-50°, and more preferably about 45° to the plane P for the blade 106. In this regard, the blade 406 is advantageous to make an angled edge, or chamfered cut, along the top surface 15 of the implant 16, preferably at the top edge 17 of the top surface 15 to provide a better fit of the implant 16 into the skull. In another embodiment, the cutter 104, such as blade 106, and the cutter 404, such as blade 406, define cutting edges 113 where the edge 113 for the cutter 104 is substantially perpendicular to the length of the tool, that is the edge 113 of the cutter 104 can be substantially perpendicular to a tool length plane extending parallel to the length of the tool, and the edge 113 for the cutter 404 is at an angle of about 30-60°, about 35-55°, about 40-50°, and more preferably about 45° to the cutting edge 113 of the cutter 104.

Surgeons and other surgical staff can use the tool of the present invention to perform a surgical procedure. The implant 16 can be inserted into a functional end of the tool to either cut the implant or shape the implant. The angled cutter or blade 406 can be used to form a chamfered along the edge 17 of the upper surface 15 of the implant 16. When the implant having a first shape has been cut and formed to its desired shape, the implant can be positioned to form a part of the patient's skull and attached into place using known techniques.

It should be noted that the illustrations and discussions of the embodiments shown in the figures are for exemplary purposes only, and should not be construed limiting the disclosure. One skilled in the art will appreciate that the present disclosure contemplates various embodiments. It should be further appreciated that the features and structures described and illustrated in accordance one embodiment can apply to all embodiments as described herein, unless otherwise indicated. Additionally, it should be understood that the concepts described above with the above-described embodiments may be employed alone or in combination with any of the other embodiments described above.

What is claimed:

1. A polymeric implant cutting tool that is configured to cut a polymeric implant, the tool comprising:
   a tool body having a length along a first direction and including a handle portion comprising an upper handle portion and a lower handle portion spaced from the upper handle portion along a second direction, substantially perpendicular to the first direction, the upper handle portion having an outer surface and an opposing inner surface and the lower handle portion having an outer surface and an opposing inner surface;
   a first cutting portion located at a distal portion of the tool body, the first cutting portion including a first cutting prong and a second cutting prong, the first cutting prong having an end and a first prong inner surface, and the second cutting prong having an end and a second prong inner surface that is spaced from the first prong inner surface along the second direction, the first cutting portion further including a first cutter having a first cutting edge to cut the implant, the first cutting edge being located longitudinally inward from the end of the first prong and the first cutter defining a substantially planar configuration that extends along a plane, wherein the plane is at an angle that is substantially perpendicular to the first direction and substantially parallel to the second direction; and
   a second cutting portion located at a proximal portion of the tool body, the second cutting portion including a third cutting prong and a fourth cutting prong, the third cutting prong having an end and a third prong inner surface, and the fourth cutting prong having an end and a fourth prong inner surface that is spaced from the third prong inner surface along the second direction, the second cutting portion further including a second cutter having a second cutting edge to cut the implant, the second cutting edge being located longitudinally inward from the end of the third prong and being positioned at an angle of between 30° and 60° from the first cutting edge,
   wherein the handle portion is between the first cutting portion and the second cutting portion.

2. The implant cutting tool according to claim 1, wherein the first and second cutters are blades.

3. The implant cutting tool according to claim 2 wherein at the location of the cutting edge of the first blade the first prong inner surface and the second prong inner surface are a distance of from 6.25 mm to 8.25 mm in the second direction and the portion of the cutting edge of the first blade that is closest to the end of the first prong is located from about 3 mm to about 20 mm from the end of the first prong.

4. The implant cutting tool according to claim 3 wherein at the location of the cutting edge of the second blade the third prong inner surface and the fourth prong inner surface are a distance of from 6.25 mm to 8.25 mm in the second direction and the portion of the cutting edge of the second blade that is closest to the end of the third prong is located from about 3 mm to about 20 mm from the end of the third prong.

5. The implant cutting tool according to claim 4 wherein the second cutting edge is positioned at an angle of between 40° and 50° from the first cutting edge.

6. The implant cutting tool according to claim 5 wherein the distance along the second direction between the inner surface of the first prong and the inner surface of the second prong is less at a location where the first blade is located than at a location closer to the second blade.

7. The implant cutting tool according to claim 6 wherein the distance along the second direction between the inner surface of the first prong and the inner surface of the second prong is less at a location where the first blade is located than at a location farther from the second blade.

8. The implant cutting tool according to claim 7 wherein the distance along the second direction between the inner surface of the third prong and the inner surface of the fourth prong is less at a location where the second blade is located than at a location closer to the first blade.

9. The implant cutting tool according to claim 8 wherein the distance along the second direction between the inner surface of the third prong and the inner surface of the fourth prong is less at a location where the second blade is located than at a location farther from the first blade.

10. The implant cutting tool of claim 1, wherein the first and second cutting prongs extend from a first end of the handle in the first direction and the third and fourth cutting prongs extend from a second end of the handle in a direction opposite the first direction.

11. The implant cutting tool of claim 1, wherein the handle portion comprises at least one handle connection portion that interconnects the upper handle portion and the lower handle portion.

12. The implant cutting tool of claim 1, wherein the handle portion defines at least first and second open spaces between the upper handle portion and the lower handle portion and between the first cutter and the second cutter, the first open space extends from the first cutter toward the second cutter, and the second open space extends from the second cutter toward the first cutter.

13. The implant cutting tool of claim 1, wherein the second cutter defines a substantially planar configuration that extends along a plane, and the plane is at an angle with respect to the first direction.

14. The implant cutting tool of claim 13, wherein the plane is at an angle of about 30-60° with respect to the first direction.

* * * * *